US008460645B2

(12) United States Patent
Lezer et al.

(10) Patent No.: US 8,460,645 B2
(45) Date of Patent: Jun. 11, 2013

(54) PROCESS FOR COATING EYELASHES

(75) Inventors: Nathalie Jager Lezer, Verrieres-le-Buisson (FR); Florence Lahousse, Thiais (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 13/209,615

(22) Filed: Aug. 15, 2011

(65) Prior Publication Data

US 2012/0042456 A1 Feb. 23, 2012

Related U.S. Application Data

(60) Provisional application No. 60/704,423, filed on Aug. 2, 2005.

(30) Foreign Application Priority Data

Jul. 22, 2005 (FR) ...................................... 05 52287

(51) Int. Cl.
 *A61Q 1/10* (2006.01)
(52) U.S. Cl.
 USPC ....................................................... 424/70.7
(58) Field of Classification Search
 None
 See application file for complete search history.

(56) References Cited

U.S. PATENT DOCUMENTS

| 2,007,245 | A | 7/1935 | Gimonet |
| 3,937,811 | A | 2/1976 | Papantoniou et al. |
| 5,162,410 | A | 11/1992 | Sweet |
| 5,874,069 | A | 2/1999 | Mendolia et al. |
| 5,919,441 | A | 7/1999 | Mendolia et al. |
| 5,925,337 | A | 7/1999 | Arraudeau et al. |
| 5,981,680 | A | 11/1999 | Petroff et al. |
| 6,051,216 | A | 4/2000 | Barr et al. |
| 6,326,012 | B1 | 12/2001 | Arnaud et al. |
| 6,372,235 | B1 | 4/2002 | Livoreil et al. |
| 6,649,173 | B1 | 11/2003 | Arnaud et al. |
| 6,835,399 | B2 | 12/2004 | Collin |
| 6,946,518 | B2 | 9/2005 | De La Poterie |
| 2002/0165297 | A1 | 11/2002 | Ferrari et al. |
| 2003/0068344 | A1 | 4/2003 | Ferrari et al. |
| 2004/0120906 | A1 | 6/2004 | Toumi et al. |
| 2004/0120920 | A1 | 6/2004 | Lion et al. |
| 2004/0146473 | A1 | 7/2004 | Lion |
| 2004/0156812 | A1 | 8/2004 | Lion |
| 2004/0234612 | A1 | 11/2004 | Blin et al. |
| 2005/0172421 | A1 | 8/2005 | Jager-Lezer et al. |
| 2005/0276779 | A1 | 12/2005 | Blin |
| 2006/0045895 | A1 | 3/2006 | Ferrari et al. |
| 2006/0093568 | A1 | 5/2006 | Blin et al. |
| 2006/0099164 | A1 | 5/2006 | De La Poterie et al. |
| 2006/0115444 | A1 | 6/2006 | Blin et al. |
| 2006/0127334 | A1 | 6/2006 | Ferrari et al. |
| 2006/0134032 | A1 | 6/2006 | Ilekti et al. |
| 2006/0134034 | A1 | 6/2006 | Blin et al. |
| 2006/0134044 | A1 | 6/2006 | Blin et al. |
| 2006/0134051 | A1 | 6/2006 | Blin et al. |

FOREIGN PATENT DOCUMENTS

| EP | 0 374 332 | | 6/1990 |
| EP | 0 847 752 | B1 | 6/1998 |
| EP | 0 979 643 | A2 | 2/2000 |
| EP | 1 068 854 | B1 | 1/2001 |
| EP | 1 086 945 | B1 | 3/2001 |
| EP | 1 249 224 | A1 | 10/2002 |
| EP | 1 396 259 | A2 | 3/2004 |
| EP | 1 411 069 | A2 | 4/2004 |
| EP | 1 477 153 | A1 | 11/2004 |
| EP | 1 600 146 | A1 | 11/2005 |
| FR | 2 232 303 | | 1/1975 |
| FR | 2 659 011 | A1 | 9/1991 |
| FR | 2 824 267 | | 11/2002 |
| FR | 2 833 163 | A1 | 6/2003 |
| FR | 2 863 493 | A1 | 6/2005 |
| WO | WO 93/23008 | | 11/1993 |
| WO | WO 02/39961 | A1 | 5/2002 |
| WO | WO 02/47630 | A1 | 6/2002 |
| WO | WO 2004/028488 | A2 | 4/2004 |
| WO | WO 2004/055079 | A2 | 7/2004 |
| WO | WO 2004/055081 | A2 | 7/2004 |
| WO | WO 2004/073626 | A2 | 9/2004 |
| WO | WO 2006/013412 | A1 | 2/2006 |

OTHER PUBLICATIONS

French Search Report for FR 0552287, dated Apr. 25, 2006.
P. Terech, "Low-molecular weight organogelators," Surfactant Organogels: Physical Context, Specialist Surfactants, Blackie Academic & Professional, pp. 209-268 (1997).
William C. Griffin, "Calculating of HLB Values of Non-ionic Surfactants," Journal of the Society of Cosmetic Chemists, vol. V, No. 4, pp. 249-256 (1954).
"Surfactants and Detersive Systems," Kirk-Othmer, Encyclopedia of Chemical Technology, Third Edition, vol. 22, John Wiley & Sons, pp. 332-432 (1983).
English language Derwent Abstract of EP 1 086 945 B1, Mar. 28, 2001.
English language Derwent Abstract of FR 2 833 163 A1, Jun. 13, 2003.

*Primary Examiner* — Jyothsna Venkat
(74) *Attorney, Agent, or Firm* — Oblon, Spivak, McClelland, Maier & Neustadt, L.L.P.

(57) ABSTRACT

The disclosure relates to a process for coating keratin fibers, comprising the application to the keratin fibers of at least one coat of at least one dry-applicable composition presented in the form of a stick. The disclosure also relates to a process for coating keratin fibers, comprising placing the fibers in contact with at least part of the surface of a stick of a dry-applicable composition, and causing a relative displacement between the surface of the stick and the fibers so as to bring about erosion of the composition and its application to the fibers in the form of a deposit of at least one coat.

23 Claims, 1 Drawing Sheet

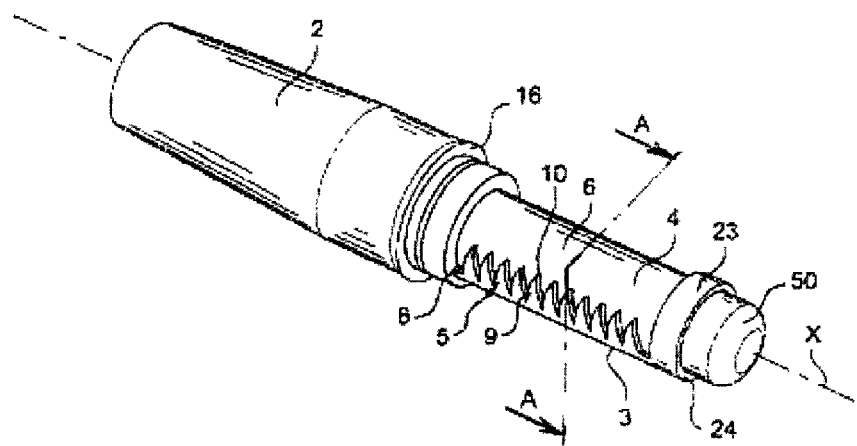

PROCESS FOR COATING EYELASHES

This application is a divisional of U.S. application Ser. No. 11/491,077, filed Jul. 24, 2006, which claims benefit of U.S. Provisional Application No. 60/704,423, filed Aug. 2, 2005, the contents of which are incorporated herein by reference, and claims benefit of priority under 35 U.S.C. §119 to French Patent Application No. FR 05 52287, filed Jul. 22, 2005, the contents of which are also incorporated herein by reference.

The present disclosure relates to a process for coating keratin fibers, such as the eyelashes, comprising applying a particular composition to the keratin fibers.

The term "keratin fibers," as used herein, means the eyelashes, the eyebrows, body hairs or head hair.

The composition may be in the form of a mascara or a product for the eyebrows. In at least one embodiment of the present disclosure, the composition is in the form of a mascara.

In the context of the present disclosure, the term "mascara" means a composition intended to be applied to the eyelashes. The mascara may be an eyelash makeup composition, an eyelash makeup base (also known as a base coat), a composition to be applied over a mascara, also known as a top coat, or a cosmetic composition for treating the eyelashes. In at least one embodiment, the mascara is used for human eyelashes, but the mascara may also be used for false eyelashes in other embodiments.

Known eyelash makeup compositions or mascaras comprise at least one wax or a mixture of waxes dispersed in an aqueous liquid phase or organic solvent. They generally have a pasty texture and are packaged in a container comprising a reservoir equipped with a drainer and an applicator, for example in the form of a brush or a comb, and are applied by taking up product from the reservoir using the applicator, passing the applicator through the drainer to remove the surplus product, and then placing the applicator impregnated with mascara in contact with the eyelashes.

Mascaras in solid form, also known as "cake mascaras," which are compositions comprising a high proportion of waxes, pigments and surfactants, which can be broken down with water, i.e., before being applied to the eyelashes, need to be placed in contact with an aqueous phase so as to partially dissolve the mascara cake, and are disclosed, for example in U.S. Pat. No. 2,007,245 and French Patent No. 2 833 163. When using cake mascaras, the application is made with a brush impregnated with water, which is placed in contact with the mascara and the mixture taken up is then applied to the eyelashes with the brush so as to deposit material onto the eyelashes.

Thus, the present disclosure relates to another formulation route for a composition for coating keratin fibers, such as the eyelashes, which may allow quick, direct and/or practical application to the eyelashes, without the use of a brush (direct transfer of material onto the eyelashes), and which is dry-applicable.

The term "dry-applicable," as used herein, means that the composition is capable of forming on keratin fibers a deposit, that can adhere and coat the fibers, without requiring any prior contact with an aqueous phase, as opposed to cake mascaras, which are erodable with water and must be partially dissolved beforehand in order to be applied to the fibers and form an adherent and coating deposit.

The composition used in the process according to the present disclosure may also have at least one good staying power property (e.g., water resistance and wear resistance) and may provide a substantial and uniform deposit of material on the eyelashes.

More specifically, the present disclosure relates to a process for coating keratin fibers, comprising the application to the keratin fibers at least one coat of at least one composition in the form of a stick, wherein the composition is dry-applicable.

According to another aspect, the present disclosure relates to a process for coating keratin fibers, comprising placing the fibers in contact with at least part of the surface of a stick of a dry-applicable composition; and causing a relative displacement between the surface of the stick and the fibers so as to bring about erosion of the composition and its application to the fibers in the form of a deposit of at least one coat.

As used herein, the term "stick" denotes a wand of predetermined form, such as cylindrical, which, in the absence of a constraint, at room temperature and atmospheric pressure, remains in its predetermined form. Thus packaged in the form of a stick, the composition may be self-supporting, such as for at least 60 seconds. Such sticks may be obtained, for example, by hot-casting the composition in a mold. The sticks may also be obtained by extrusion.

In at least one embodiment, the composition packaged in stick form has a hardness ranging from 500 to 18,200 Pa.

In at least one further embodiment, the composition has a hardness ranging from 900 to 10,000 Pa, such as from 1800 to 8200 Pa.

With such a hardness, the texture may be "soft" enough to allow direct and easy application to the eyelashes, such as a deposit of material by simply placing the composition in contact with the eyelashes, without exerting undue pressure on the eyelash fringe.

To determine the hardness of a stick in accordance with the present disclosure, the "cheese wire" method may be used, which comprises cutting the stick transversely using a rigid tungsten wire 250 μm in diameter, by advancing the wire relative to the stick at a speed of 100 mm/min. The hardness corresponds to the maximum shear force exerted by the wire on the stick at 20° C., this force being measured using a DFGS2 tensile testing machine sold by the company Indelco-Chatillon. The measurement is repeated 6 times and the mean is then determined. The mean of the 6 values read using the tensile testing machine mentioned above, which is noted Y, is given in grams. This mean value is converted into pascals by means of the equation below, to obtain the hardness value:

$$(Y \times 10^{-3} \times 9.8)/\text{area of the transverse section of the stick (in m}^2).$$

In the case of a cylindrical stick of circular cross section, the area of the transverse section is equal to $\pi \times R^2$, R being the radius of the stick expressed in meters.

According to this method, the hardness of a cosmetic composition in accordance with at least one embodiment of the present disclosure presented in stick form ranges, to within 10%, from 500 to 18,200 Pa, such as, for example, from 900 to 10,000 Pa or from 1800 to 8200 Pa.

The composition used in the process according to the present disclosure may comprise a liquid fatty phase and at least one agent for structuring the liquid fatty phase, via which the hardness of the composition is adjusted.

BRIEF DESCRIPTION OF THE DRAWING

FIG. 1 illustrates a packaging and application device using the composition as disclosed herein.

Liquid Fatty Phase

For the purposes of the present disclosure, the term "liquid fatty phase" means a fatty phase that is liquid at room temperature (25° C.) and atmospheric pressure (760 mmHg), composed of at least one mutually compatible non-aqueous fatty substance that is liquid at room temperature, also known as an oil.

The at least one oil may be chosen from volatile oils and/or non-volatile oils, and mixtures thereof.

The at least one oil may be present in the composition according to at least one embodiment of the present disclosure in an amount ranging from 5% to 85% by weight, such as, for example, from 10% to 70% or from 15% to 60% by weight, relative to the total weight of the composition.

For the purposes of the present disclosure, the term "volatile oil" means an oil that is capable of evaporating on contact with the skin or the keratin fiber in less than one hour, at room temperature and atmospheric pressure. Volatile organic solvents and volatile oils according to the present disclosure are volatile organic solvents and cosmetic oils that are liquid at room temperature, with a non-zero vapor pressure at room temperature and atmospheric pressure, for example, ranging from 0.13 Pa to 40,000 Pa ($10^{-3}$ to 300 mmHg), from 1.3 Pa to 13,000 Pa (0.01 to 100 mmHg), or from 1.3 Pa to 1300 Pa (0.01 to 10 mmHg). As used herein, the term "non-volatile oil" means an oil that remains on the skin or the keratin fiber at room temperature and atmospheric pressure for at least several hours and, for example, has a vapor pressure of less than $10^{-3}$ mmHg (0.13 Pa).

In at least one embodiment, these oils may be chosen from hydrocarbon-based oils, silicone oils or fluoro oils, or mixtures thereof.

In the context of the present disclosure, the term "hydrocarbon-based oil" means an oil mainly containing hydrogen and carbon atoms and optionally oxygen, nitrogen, sulfur or phosphorus atoms. The volatile hydrocarbon-based oils may be chosen from hydrocarbon-based oils containing from 8 to 16 carbon atoms, such as branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names ISOPAR or PERMETHYL, branched $C_8$-$C_{16}$ esters and isohexyl neopentanoate, and mixtures thereof. Other volatile hydrocarbon-based oils, for instance petroleum distillates, including those sold under the name SHELL SOLT by the company Shell, may also be used. In at least one embodiment of the present disclosure, the volatile solvent may be chosen from volatile hydrocarbon-based oils containing from 8 to 16 carbon atoms, and mixtures thereof.

Among volatile oils that may also be used according to the present disclosure, non-limiting mention may be made of volatile silicones, for instance volatile linear or cyclic silicone oils, including those with a viscosity $\leq 8$ centistokes ($8 \times 10^{-6}$ m²/s) and those containing from 2 to 7 silicon atoms, these silicones optionally comprising alkyl or alkoxy groups containing from 1 to 10 carbon atoms. Among volatile silicone oils that may be used according to at least one embodiment of the disclosure, non-limiting mention may be made of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethyl-pentasiloxane, and mixtures thereof.

Non-limiting mention may also be made of the linear volatile alkyltrisiloxane oils of formula (I):

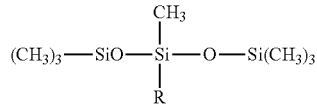

wherein R is chosen from alkyl groups comprising 2 to 4 carbon atoms and of which at least one hydrogen atom may be substituted with at least one fluorine or chlorine atom.

Among the oils of formula (I) that may be used according to at least one embodiment of the present disclosure, non-limiting mention may be made of:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) wherein R is, respectively, a butyl group, a propyl group and an ethyl group.

Volatile fluorinated solvents such as nonafluoromethoxybutane or perfluoromethylcyclopentane may also be used.

According to at least one embodiment, the composition comprises a volatile oil or a mixture of volatile oils, or a volatile liquid fatty phase, having in the composition an evaporation profile such that the mass of volatile oil(s) evaporated after thirty minutes ranges from 1.7 to 370 mg/cm², such as, for example, from 2 to 70 mg/cm² or from 2 to 30 mg/cm².

The evaporation profile is measured according to the following protocol:

15 g of oil or of the mixture of oils to be tested are placed in a crystallizing dish (diameter: 7 cm) placed on a balance which is in a chamber of about 0.3 m² with controlled temperature (25° C.) and hygrometry (50% relative humidity). The liquid is left to evaporate freely, without stirring, ventilation being provided using a fan (Papst-Motoren, reference 8550 N, spinning at 2700 rpm) placed vertically above the crystallizing dish containing the solvent, the vanes being directed towards the crystallizing dish and 20 cm away from the base of the crystallizing dish. The mass of oil(s) remaining in the crystallizing dish is measured at regular intervals, such as every 30 minutes. The evaporation rates are expressed as mg of oil evaporated per unit area (cm²) and per unit of time (minutes).

In at least one embodiment, the composition comprises at least one volatile oil chosen from hydrocarbon-based volatile oils containing from 8 to 16 carbon atoms, volatile silicone oils containing from 2 to 7 silicon atoms, and mixtures thereof.

The composition may also comprise at least one non-volatile oil, chosen, for example, from non-volatile hydrocarbon-based oils and/or silicone oils and/or fluoro oils.

Among non-volatile hydrocarbon-based oils that may be used according to at least one embodiment of the present disclosure, non-limiting mention may be made of:

hydrocarbon-based oils of plant origin, such as triesters of fatty acids and of glycerol, the fatty acids of which may have varied chain lengths from $C_4$ to $C_{24}$, these chains possibly being linear or branched, and saturated or unsaturated; these oils may be chosen from, for example, wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, marrow oil, blackcurrant oil, evening primrose oil, millet oil, barley oil, quinoa oil, rye oil, safflower oil, candlenut oil, passionflower oil and musk rose oil; or caprylic/capric acid triglycerides, for instance those sold by the company Stéarineries Dubois or those sold under the names MIGLYOL 810, 812 and 818 by the company Dynamit Nobel;
synthetic ethers comprising 10 to 40 carbon atoms;

linear and branched hydrocarbons of mineral or synthetic origin, such as petroleum jelly, polydecenes, hydrogenated polyisobutene such as parleam, and squalane, and mixtures thereof;

synthetic esters, for instance oils of formula $R_1COOR_2$ wherein $R_1$ is chosen from linear and branched fatty acid residues comprising 1 to 40 carbon atoms and $R_2$ is chosen from hydrocarbon-based chains, which may be branched, containing from 1 to 40 carbon atoms, on condition that $R_1+R_2 \geqq 10$ carbon atoms, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, alcohol or polyalcohol octanoates, decanoates or ricinoleates, for instance propylene glycol dioctanoate; hydroxylated esters, for instance isostearyl lactate or diisostearyl malate; and pentaerythritol esters;

fatty alcohols that are liquid at room temperature with a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

higher fatty acids such as oleic acid, linoleic acid or linolenic acid;

carbonates;

acetates;

citrates;

and mixtures thereof.

Non-volatile silicone oils that may be used in the composition according to the present disclosure may be non-volatile polydimethylsiloxanes (PDMS), polydimethyl-siloxanes comprising alkyl or alkoxy groups, which are pendent and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyltrimethylsiloxysilicates.

In at least one embodiment, fluoro oils that may be used in the present disclosure may be chosen from fluorosilicone oils, fluoro polyethers and fluorosilicones as described in European Patent No. EP-A-0 847 752.

According to at least one embodiment, the fatty phase may comprise an ester oil. This ester oil may be chosen from the esters of monocarboxylic acids with monoalcohols and polyalcohols.

In at least one embodiment, the ester is chosen from compounds of formula (II) below:

$$R_1\text{—CO—O—}R_2 \quad (II)$$

wherein:

$R_1$ is chosen from linear and branched alkyl radicals of 1 to 40 carbon atoms, for example 7 to 19 carbon atoms, optionally comprising at least one ethylenic double bond, and optionally substituted, and $R_2$ is chosen from linear and branched alkyl radicals of 1 to 40 carbon atoms, for example 3 to 30 carbon atoms or 3 to 20 carbon atoms, optionally comprising at least one ethylenic double bond, and optionally substituted.

The term "optionally substituted," as used herein, means that $R_1$ and/or $R_2$ can comprise at least one substituent chosen, for example, from groups comprising at least one hetero atom chosen from O, N and S, such as amino, amine, alkoxy and hydroxyl.

In at least one embodiment, the total number of carbon atoms of $R_1+R_2$ is $\geqq 9$.

$R_1$ may be chosen from residues of linear and branched fatty acids, including higher fatty acids, containing from 1 to 40, for example, from 7 to 19 carbon atoms, and $R_2$ may be chosen from linear and branched hydrocarbon-based chains containing from 1 to 40, such as, for example, from 3 to 30 or from 3 to 20 carbon atoms. In at least one embodiment, the number of carbon atoms of $R_1+R_2 \geqq 9$.

Non-limiting examples of groups $R_1$ include those derived from fatty acids chosen from acetic acid, propionic acid, butyric acid, caproic acid, caprylic acid, pelargonic acid, capric acid, undecanoic acid, lauric acid, myristic acid, palmitic acid, stearic acid, isostearic acid, arachidic acid, behenic acid, oleic acid, linolenic acid, linoleic acid, oleostearic acid, arachidonic acid and erucic acid, and mixtures thereof.

Non-limiting examples of esters include purcellin oil (cetostearyl octanoate), isononyl isononanoate, isopropyl myristate, 2-ethylhexyl palmitate, 2-octyldodecyl stearate, 2-octyldodecyl erucate, isostearyl isostearate, and heptanoates, octanoates, decanoates or ricinoleates of alcohols or polyalcohols, for example of fatty alcohols.

In at least one embodiment, the esters are chosen from the compounds of formula (I) above, wherein $R_1$ is chosen from unsubstituted linear and branched alkyl groups of 1 to 40 carbon atoms, such as 7 to 19 carbon atoms, optionally comprising at least one ethylenic double bond, and $R_2$ is chosen from unsubstituted linear and branched alkyl group of 1 to 40 carbon atoms, such as 3 to 30 carbon atoms or 3 to 20 carbon atoms, optionally comprising at least one ethylenic double bond.

In at least one embodiment, $R_1$ is chosen from unsubstituted branched alkyl groups of 4 to 14 carbon atoms, for example 8 to 10 carbon atoms, and $R_2$ is chosen from unsubstituted branched alkyl groups of 5 to 15 carbon atoms, such as 9 to 11 carbon atoms. In at least one embodiment of the present disclosure, in formula (I), $R_1$—CO— and $R_2$ have the same number of carbon atoms and are derived from the same radical, such as an unsubstituted branched alkyl, for example isononyl, i.e., wherein the ester oil molecule is symmetrical.

In at least one embodiment of the present disclosure, the ester oil is chosen from the following compounds:

isononyl isononanoate,
cetostearyl octanoate,
isopropyl myristate,
2-ethylhexyl palmitate,
2-octyldodecyl stearate,
2-octyldodecyl erucate,
isostearyl isostearate,
and mixtures thereof.

The liquid fatty phase may be present in an amount ranging from 5% to 85% by weight, such as from 10% to 70% or from 15% to 60% by weight, relative to the total weight of the composition.

Structuring Agent

The composition according to the present disclosure may comprise at least one agent for structuring the liquid fatty phase (formed from the volatile or non-volatile organic solvents or oils described above), chosen from waxes, semicrystalline polymers and lipophilic gelling agents, and mixtures thereof.

The structuring agent may be present in an amount ranging from 1% to 50% by weight, such as, for example, from 5% to 20% or from 7.5% to 17% by weight, relative to the total weight of the composition.

The amount of oily structuring agent may be adjusted by a person skilled in the art as a function of the structuring properties of the agents.

Wax

In the context of the present disclosure, a wax is defined as a lipophilic compound that is solid at room temperature (25° C.) which may or may not be deformable, with a solid/liquid reversible change of state, having a melting point of greater than or equal to 30° C., which may be up to 200° C., and, for example, may be up to 120° C.

By bringing the wax to the liquid form (melting), it may be possible to make it miscible with oils and to form a microscopically uniform mixture, but on cooling the mixture to room temperature, recrystallization of the wax in the oils of the mixture may be obtained.

In at least one embodiment, waxes that are suitable for the present disclosure may have a melting point of greater than or equal to 45° C., such as greater than or equal to 55° C.

For the purposes of the present disclosure, the melting point corresponds to the temperature of the most endothermic peak observed by thermal analysis (DSC) as described in ISO standard 11357-3; 1999. The melting point of the wax may be measured using a differential scanning calorimeter (DSC), for example the calorimeter sold under the name MDSC 2920 by the company TA Instruments.

The measuring protocol is as follows:

A sample of 5 mg of wax placed in a crucible is subjected to a first temperature rise ranging from −20° C. to 100° C., at a heating rate of 10° C./minute. It is then cooled from 100° C. to −20° C. at a cooling rate of 10° C./minute and is finally subjected to a second temperature increase ranging from −20° C. to 100° C. at a heating rate of 5° C./minute. During the second temperature increase, the variation of the difference in power absorbed by the empty crucible and by the crucible containing the sample of wax is measured as a function of the temperature. The melting point of the compound is the temperature value corresponding to the top of the peak of the curve representing the variation in the difference in absorbed power as a function of the temperature.

Waxes that may be used in the compositions according to at least one embodiment of the disclosure are chosen from waxes that are solid at room temperature of animal, plant, mineral or synthetic origin, and mixtures thereof.

Waxes that may be used in the compositions according to at least one embodiment of the disclosure have a hardness ranging from 0.5 MPa to 15 MPa, such as, for example, from 1 MPa to 15 MPa.

The hardness is determined by measuring the compression force, measured at 20° C. using the texturometer sold under the name TA-XT2 by the company Rheo, equipped with a stainless-steel cylindrical spindle 2 mm in diameter, travelling at a measuring speed of 0.1 mm/second, and penetrating the wax to a penetration depth of 0.3 mm.

The measuring protocol is as follows:

The wax is melted at a temperature equal to the melting point of the wax +10° C. The molten wax is poured into a container 25 mm in diameter and 20 mm deep. The wax is recrystallized at room temperature (25° C.) for 24 hours such that the surface of the wax is flat and smooth, and the wax is then stored for at least 1 hour at 20° C. before measuring the hardness or the tack.

The texturometer spindle is displaced at a speed of 0.1 mm/s then penetrates the wax to a penetration depth of 0.3 mm. When the spindle has penetrated the wax to a depth of 0.3 mm, the spindle is held still for 1 second (corresponding to the relaxation time) and is then withdrawn at a speed of 0.5 mm/s.

The hardness value is the maximum compression force measured divided by the area of the texturometer cylinder in contact with the wax.

The composition may comprise at least one wax chosen from:
"structuring" waxes that have little affinity for the liquid fatty phase of the composition,
"non-structuring" waxes that have affinity for the liquid fatty phase of the composition,
and mixtures thereof.

The "structuring" or "non-structuring" nature of the wax is defined from the hardness value obtained on a binary mixture consisting of 15% wax and 85% of the oil(s) of the liquid fatty phase of the composition.

The hardness of the binary mixture is measured according to the following protocol:

The wax is melted at a temperature about 10° C. above the melting point of the wax, with stirring using a magnetic bar, and, after the wax has totally melted, the oil(s) is (are) then added. Stirring with the magnetic bar is continued for 30 minutes.

The mixture is poured into an aluminum mold preheated to 42° C. and left to stand for 10 minutes at 25° C., the assembly is placed at −28° C. for 20 minutes and is then removed from the mold and packaged in packaging 12.3 mm in diameter, which is kept at a temperature of 20° C. for 24 hours before performing the measurement.

The hardness is measured using the "cheese wire" method, which comprises cutting the stick transversely using a rigid tungsten wire 250 µm in diameter, by advancing the wire relative to the stick at a speed of 100 mm/min. The hardness corresponds to the maximum shear force exerted by the wire on the stick at 20° C., this force being measured using a DFGS2 tensile testing machine sold by the company Indelco-Chatillon. The measurement is repeated 6 times and the mean is then determined. The hardness is expressed in grams.

A wax whose binary mixture as defined above has a hardness of greater than or equal to 35 g (±2 g) is considered as structuring.

In contrast, a wax whose binary mixture as defined above has a hardness of less than 35 g (±2 g) is considered as non-structuring.

The hardness of the composition may be modified by appropriately selecting the structuring and non-structuring waxes as a function of the hardness of the wax-oil binary mixture.

In at least one embodiment, the composition comprises at least one structuring wax and at least one non-structuring wax, which may be present in a structuring wax/non-structuring wax ratio ranging from 5/95 to 50/50, such as, for example, from 10/90 to 40/60 or from 15/85 to 35/65.

In at least one embodiment, the structuring and/or non-structuring waxes may be chosen from protic waxes and aprotic waxes, and mixtures thereof.

Aprotic Wax

As used herein, the term "aprotic wax" means a wax comprising few or no hydrogen atoms linked to a highly electronegative atom such as O or N.

In at least one embodiment, aprotic waxes are chosen from apolar waxes, i.e., waxes consisting solely of molecules comprising only carbon and hydrogen atoms in their chemical structure, in other words comprising no hetero atoms (such as O, N or P).

Non-limiting examples of aprotic waxes, including apolar waxes, which may be mentioned include paraffin waxes, microcrystalline waxes, ozokerite, ceresin and synthetic waxes, for instance polymethylene wax, polyethylene wax, propylene wax and ethylene/propylene copolymers thereof, or alternatively Fischer-Tropsch waxes, and mixtures thereof.

The waxes obtained by esterification or modified by esterification and which may comprise residual OH groups as a function of the esterification yield may be considered as aprotic within the meaning of the present disclosure. Such waxes are, for example, the wax obtained from the reaction of a fatty acid with a branched polyol of bis(trimethylol) type, for instance those sold under the name HEST by the company Heterene. Non-limiting mention may also be made of silicone-modified waxes, for instance the silicone-treated candelilla wax sold by Koster Keunen under the name Siliconyl candelilla.

The waxes obtained by catalytic hydrogenation of animal or plant oils containing linear or branched $C_8$-$C_{32}$ fatty chains, such as hydrogenated jojoba oil, hydrogenated sunflower oil or hydrogenated coconut oil, or the wax obtained by hydrogenation of olive oil esterified with stearyl alcohol, may also be considered as aprotic.

In at least one embodiment of the present disclosure, the aprotic wax is chosen from microcrystalline waxes, paraffin waxes, polyethylene waxes, including the wax sold under the reference Wax AC 617 by the company Honeywell, and mixtures thereof.

Protic Wax

Waxes that are considered protic waxes are hydrocarbon-based waxes, for instance beeswax or lanolin wax; orange wax, lemon wax, rice bran wax, carnauba wax, candelilla wax, ouricurry wax, Japan wax, berry wax, shellac wax and sumach wax; montan wax, hydrogenated castor oil, hydrogenated lanolin oil, the waxes obtained from the reaction of fatty acids with carbohydrates, for instance disaccharides of sucrose type, such as sucrose polybehenate, sold by Croda under the name CROMADERM B, and hydroxy ester waxes, for instance $C_{20}$-$C_{40}$ alkyl (hydroxystearyloxy)stearate wax, such as those sold under the names "Kester Wax K 82 P®" and "Kester Wax K 80 P®" by the company Koster Keunen. Non-limiting mention may also be made of fatty alcohol waxes chosen from saturated and unsaturated, branched and unbranched fatty alcohols containing from 20 to 60 carbon atoms or mixtures comprising at least 30% of the fatty alcohols, for example with polyethylene, for instance the wax sold under the reference Performacol® 550 L by the company New Phase Technologies.

In at least one embodiment, the protic wax is chosen from beeswax and fatty alcohol waxes containing from 20 to 60 carbon atoms, and mixtures thereof.

According to at least one embodiment, the composition according to the present disclosure comprises at least one protic wax, which is, for example, a polar wax, and at least one aprotic wax, which is for example, an apolar wax, chosen from the waxes mentioned above.

According to at least one embodiment of the present disclosure, the composition comprises at least one liquid fatty phase comprising at least one volatile hydrocarbon-based oil chosen from isoparaffins containing from 8 to 16 carbon atoms, such as, for example, isododecane, at least one aprotic wax, chosen, for example, from polyethylene waxes, which is non-structuring, and at least one polar wax chosen from fatty alcohol waxes, which is structuring.

According to at least one other embodiment of the present disclosure, the composition comprises at least one liquid fatty phase comprising at least one volatile silicone oil chosen from volatile cyclic silicone oils, such as those with a viscosity $\leq 8$ centistokes ($8 \times 10^{-6}$ m$^2$/s), and, for example, cyclopentadimethylsiloxane, at least one aprotic wax, which may be apolar, chosen from polyethylene wax, which is structuring on account of its affinity for silicone oils, and at least one protic wax, which may be polar, chosen from beeswax, which is non-structuring.

In at least one embodiment, the structuring and non-structuring waxes may be present in an amount ranging from 1% to 30% by weight, such as, for example, from 5% to 20% or from 7.5% to 17% by weight, relative to the total weight of the composition.

Semi-Crystalline Polymers

As used herein, the term "polymer" means compounds containing at least two repeating units, for example at least three repeating units or at least ten repeating units. In the context of the present disclosure, the term "semi-crystalline polymer" means polymers comprising a crystallizable portion, a crystallizable side chain or a crystallizable block in the skeleton, and an amorphous portion in the skeleton and having a first-order reversible phase-change temperature, such as melting (solid-liquid transition). When the crystallizable portion is in the form of a crystallizable block of the polymer skeleton, the amorphous portion of the polymer may be in the form of an amorphous block; in this case, the semi-crystalline polymer is a block copolymer, for example, of the diblock, triblock or multiblock type, comprising at least one crystallizable block and at least one amorphous block. In the present disclosure, the term "block" means at least five identical repeating units. The crystallizable block is of chemical nature different than that of the amorphous block.

The semi-crystalline polymer has a melting point of greater than or equal to 30° C. (e.g., ranging from 30° C. to 80° C.), and in at least one embodiment has a melting point ranging from 30° C. to 60° C. This melting point is a first-order change of state temperature.

The melting point may be measured by any known method, such as using a differential scanning calorimeter (DSC).

In at least one embodiment, the semi-crystalline polymer has a number-average molecular mass of greater than or equal to 1000. In at least one further embodiment, the semi-crystalline polymer of the composition of the present disclosure has a number-average molecular mass $\overline{M}n$ ranging from 2000 to 800,000, such as, for example, from 3000 to 500,000, or from 4000 to 150,000, or it may have a number-average molecular mass less than 100,000, such as from 4000 to 99,000. In at least one embodiment, the semi-crystalline polymer has a number-average molecular mass of greater than 5600, for example ranging from 5700 to 99,000.

For the purposes of the present disclosure, the term "crystallizable chain or block" means a chain or block which, if it were alone, would reversibly change from the amorphous state to the crystalline state, depending on whether the system is above or below the melting point. For the purposes of the present disclosure, a "chain" is a group of atoms, which is pendent or lateral relative to the polymer skeleton. A "block" is a group of atoms belonging to the skeleton, this group constituting one of the repeating units of the polymer. In at least one embodiment, the "crystallizable side chain" may be a chain containing at least six carbon atoms.

The semi-crystalline polymer may be chosen from block copolymers comprising at least one crystallizable block and at least one amorphous block, and homopolymers and copolymers bearing at least one crystallizable side chain per repeating unit, and mixtures thereof.

Such polymers are described, for example, in European Patent No. EP 1 396 259.

In at least one embodiment of the present disclosure, the polymer is derived from a monomer containing a crystallizable chain chosen from saturated $C_{14}$-$C_{22}$ alkyl (meth)acrylates.

As an example of a semi-crystalline polymer that may be used in the composition according to the present disclosure, non-limiting mention may be made of the Intelimer® products from the company Landec described in the brochure "Intelimer® Polymers", Landec IP22 (Rev. 4-97). These polymers are in solid form at room temperature (25° C.) and bear crystallizable side chains.

Lipophilic Gelling Agents

Gelling agents that may be used in the compositions according to the present disclosure may be organic or mineral, polymeric or molecular lipophilic gelling agents.

Among mineral lipophilic gelling agents that may be used according to at least one embodiment of the present disclosure, non-limiting mention may be made of optionally modified clays, for instance hectorites modified with a $C_{10}$ to $C_{22}$ fatty acid ammonium chloride, for instance hectorite modified with distearyldimethylammonium chloride, for instance the product sold under the name Bentone 38V® by the company Elementis.

Non-limiting mention may also be made of fumed silica optionally subjected to a hydrophobic surface treatment, the particle size of which is less than 1 rim. In at least one embodiment, the surface of the silica may be chemically modified by chemical reaction generating a reduced number of silanol groups present at the surface of the silica. In at least one embodiment, silanol groups can be substituted with hydrophobic groups: a hydrophobic silica is then obtained. The hydrophobic groups may be:

trimethylsiloxyl groups, which are obtained, for example, by treating fumed silica in the presence of hexamethyl-disilazane. Silicas thus treated are known as "silica silylate" according to the CTFA (6th edition, 1995). They are sold, for example, under the references Aerosil R812® by the company Degussa, and Cab-O-Sil TS-530® by the company Cabot;

dimethylsilyloxyl or polydimethylsiloxane groups, which are obtained, for example, by treating fumed silica in the presence of polydimethylsiloxane or dimethyldichlorosilane. Silicas thus treated are known as "silica dimethyl silylate" according to the CTFA (6th edition, 1995). They are sold, for example, under the references Aerosil R972® and Aerosil R974® by the company Degussa, and Cab-O-Sil TS-610® and Cab-O-Sil TS-720® by the company Cabot.

In at least one embodiment, the hydrophobic fumed silica has a particle size that may be nanometric to micrometric, for example ranging from about 5 to 200 nm.

It is also possible to use non-polymeric, molecular organic gelling agents, also known as organogelling agents, associated with a liquid fatty phase (which may be the liquid fatty phase of the composition according to the present disclosure), which are compounds whose molecules are capable of establishing between themselves physical interactions leading to self-aggregation of the molecules with formation of a supramolecular 3D network that is responsible for the gelation of the liquid fatty phase.

The supramolecular network may result from the formation of a network of fibrils (caused by the stacking or aggregation of organogelling molecules), which immobilizes the molecules of the liquid fatty phase.

The ability to form this network of fibrils, and thus to gel, depends on the nature (or chemical class) of the organogelling agent, on the nature of the substituents borne by its molecules for a given chemical class, and on the nature of the liquid fatty phase.

The physical interactions are of diverse nature but exclude co-crystallization. These physical interactions may be, for example, interactions of self-complementary hydrogen interaction type, π interactions between unsaturated rings, dipolar interactions, coordination bonds with organometallic derivatives, and combinations thereof. Each molecule of an organogelling agent can establish several types of physical interaction with a neighboring molecule. Thus, for example, the molecules of the organogelling agents according to the present disclosure can comprise at least one group capable of establishing hydrogen bonds, such as, for example, at least two groups, at least one aromatic ring, at least two aromatic rings, at least one ethylenically unsaturated bonds and/or at least one asymmetric carbons. In at least one embodiment, the groups capable of forming hydrogen bonds are chosen from hydroxyl, carbonyl, amine, carboxylic acid, amide, urea and benzyl groups, and combinations thereof.

Organogelling agents according to the present disclosure can be soluble in the liquid fatty phase after heating to obtain a transparent uniform liquid phase. They may be solid or liquid at room temperature and atmospheric pressure.

Molecular organogelling agents that may be used in the composition according to at least one embodiment of the present disclosure may be chosen from those described in the document "Specialist Surfactants" edited by D. Robb, 1997, pp. 209-263, Chapter 8 by P. Terech, European Patent Application Nos. EP-A-1 068 854 and EP-A-1 086 945, or International Patent Application No. WO 02/47031.

Non-limiting mention may be made, among these organogelling agents, of amides of carboxylic acids, such as tricarboxylic acids, for instance cyclohexanetricarboxamides (see European Patent Application No. EP-A-1 068 854), diamides with hydrocarbon-based chains each containing from 1 to 22 carbon atoms, for example from 6 to 18 carbon atoms, the chains being unsubstituted or substituted with at least one substituent chosen from ester, urea and fluoro groups (see European Patent Application No. EP-A-1 086 945) and diamides resulting from the reaction of diaminocyclohexane, such as diaminocyclohexane in trans form, and of an acid chloride, for instance N,N'-bis(dodecanoyl)-1,2-diaminocyclohexane, N-acylamino acid amides, for instance the diamides resulting from the action of an N-acylamino acid with amines containing from 1 to 22 carbon atoms, for instance those described in International Patent Application No. WO 93/23008 and, for example, N-acylglutamic acid amides wherein the acyl group is chosen from $C_8$ to $C_{22}$ alkyl chains, such as N-lauroyl-L-glutamic acid dibutylamide, manufactured or sold by the company Ajinomoto under the name GP-1, and mixtures thereof.

The polymeric organic lipophilic gelling agents are, for example:

partially or totally crosslinked elastomeric organopolysiloxanes of three-dimensional structure, for instance those sold under the names KSG6®, KSG16® and KSG18® from Shin-Etsu, Trefil E-505C® or Trefil E-506C® from Dow Corning, Gransil SR-CYC®, SR DMF 10®, SR-DC556®, SR 5CYC gel®, SR DMF 10 gel® and SR DC 556 gel® from Grant Industries and SF 1204® and JK 113® from General Electric;

ethylcellulose, for instance the product sold under the name Ethocel® by Dow Chemical;

polycondensates of polyamide type resulting from condensation between (α) at least one acid chosen from dicarboxylic acids containing at least 32 carbon atoms, such as fatty acid dimers, and (β) an alkylenediamine and, for example, ethylenediamine, in which the polyamide polymer comprises at least one carboxylic acid end group esterified or amidated with at least one saturated and linear monoalcohol or one saturated and linear monoamine containing from 12 to 30 carbon atoms, and, for example, copolymers such as the products sold under the Uniclear names by the company Arizona Chemical;

silicone polyamides of the polyorganosiloxane type such as those described in U.S. Pat. Nos. 5,874,069, 5,919,441, 6,051,216 and 5,981,680, for instance those sold under the reference Dow Corning 2-8179 GELLANT by the company Dow Corning;

galactomannans containing from one to six hydroxyl groups per saccharide, such as from two to four hydroxyl groups per saccharide, substituted with a saturated or unsaturated alkyl chain, for instance guar gum alkylated with $C_1$-$C_6$ alkyl chains, such as $C_1$-$C_3$ alkyl chains, and mixtures thereof;

optionally hydrogenated block copolymers, of "diblock", "triblock" or "radial" type, such as those containing styrene blocks and ethylene/$C_3$-$C_4$ alkylene blocks.

Among examples of diblock copolymers, which may be hydrogenated, that may be used according to the present disclosure, non-limiting mention may be made of styrene-ethylene/propylene copolymers and styrene-ethylene/butadiene copolymers. Diblock copolymers are sold, for example, under the name Kraton® G1701E by the company Kraton Polymers.

Among examples of triblock copolymers, which may be hydrogenated, that may be used according to the present disclosure, non-limiting mention may be made of styrene-ethylene/propylene-styrene copolymers, styrene-ethylene/butadiene-styrene copolymers, styrene-isoprene-styrene copolymers and styrene-butadiene-styrene copolymers. Triblock polymers are sold, for example, under the names Kraton® G1650, Kraton® G1652, Kraton® D1101, Kraton® D1102 and Kraton® D1160 by the company Kraton Polymers.

It is also possible to use a mixture of hydrogenated styrene-butylene/ethylene-styrene triblock copolymer and of hydrogenated ethylene-propylene-styrene star polymer, such a mixture being, for example, in isododecane. Such mixtures are sold, for example, by the company Penreco under the trade names Versagel® M5960 and Versagel® M5670.

Non-limiting mention may also be made of polystyrene/polyisoprene or polystyrene/polybutadiene copolymers such as those sold under the name Luvitol HSB® by the company BASF.

Among the lipophilic gelling agents that may be used in the compositions according to the present disclosure, non-limiting mention may also be made of fatty acid esters of dextrin, such as dextrin palmitates, including the products sold under the name Rheopearl TL® or Rheopearl KL® by the company Chiba Flour.

Pasty Compound

In at least one embodiment, the composition according to the present disclosure may comprise at least one pasty compound.

For the purposes of the present disclosure, the term "pasty" denotes a lipophilic fatty compound that undergoes a reversible solid/liquid change of state and that comprises, at a temperature of 23° C., a liquid fraction and a solid fraction.

In at least one embodiment, the pasty compound has a hardness at 20° C. ranging from 0.001 to 0.5 MPa, such as from 0.002 to 0.4 MPa.

The hardness is measured according to a method of penetration of a probe in a sample of compound and in particular using a texture analyzer (for example the TA-XT2I machine from Rheo) equipped with a stainless-steel cylinder 2 mm in diameter. The hardness measurement is performed at 20° C. at the center of five samples. The cylinder is introduced into each sample at a pre-speed of 1 mm/s and then at a measuring speed of 0.1 mm/s, the penetration depth being 0.3 mm. The hardness value revealed is that of the maximum peak.

This pasty compound may also, at a temperature of 23° C., be in the form of a liquid fraction and a solid fraction. In other words, the starting melting point of the pasty compound may be less than 23° C. The liquid fraction of the pasty compound measured at 23° C. is present in an amount ranging from 23% to 97% by weight of the compound. In at least one embodiment, this liquid fraction at 23° C. is present in an amount ranging from 40% to 85% by weight of the compound.

The liquid fraction by weight of the pasty compound at 23° C. is equal to the ratio of the heat of fusion consumed at 23° C. to the heat of fusion of the pasty compound.

The heat of fusion of the pasty compound is the heat consumed by the compound to change from the solid state to the liquid state. The pasty compound is said to be in the solid state when all of its mass is in solid form. The pasty compound is said to be in the liquid state when all of its mass is in liquid form.

The heat of fusion of the pasty compound is equal to the area under the curve of the thermogram obtained using a differential scanning calorimeter (DSC), such as the calorimeter sold under the name MDSC 2920 by the company TA Instrument, with a temperature rise of 5 or 10° C. per minute, according to standard ISO 11357-3:1999. The heat of fusion of the pasty compound is the amount of energy required to make the compound change from the solid state to the liquid state. It is expressed in J/g.

The heat of fusion consumed at 23° C. is the amount of energy absorbed by the sample to change from the solid state to the state that it has at 23° C., comprising a liquid fraction and a solid fraction.

In at least one embodiment, the liquid fraction of the pasty compound, measured at 32° C., ranges from 40% to 100% by weight of the compound, such as, for example, from 50% to 100%, from 80% to 100%, or from 90% to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the heat of fusion consumed at 32° C. to the heat of fusion of the pasty compound. The heat of fusion consumed at 32° C. is calculated in the same manner as the heat of fusion consumed at 23° C.

In at least one embodiment, the pasty compound is chosen from synthetic compounds and compounds of plant origin. A pasty compound may be obtained by synthesis from starting materials of plant origin.

According to at least one embodiment of the present disclosure, the pasty compound is chosen from:
lanolin and derivatives thereof,
polymer or non-polymer silicone compounds,
polymer or non-polymer fluoro compounds,
vinyl polymers, such as:
  olefin homopolymers
  olefin copolymers
  hydrogenated diene homopolymers and copolymers
  linear or branched oligomers, which are homopolymers or copolymers of alkyl (meth)acrylates, including those containing a $C_8$-$C_{30}$ alkyl group
  oligomers, which are homopolymers and copolymers of vinyl esters containing $C_8$-$C_{30}$ alkyl groups
  oligomers, which are homopolymers and copolymers of vinyl ethers containing $C_8$-$C_{30}$ alkyl groups, liposoluble polyethers resulting from the polyetherification between at least one $C_2$-$C_{100}$ diol, such as $C_2$-$O_{50}$ diols,
esters and polyesters,
and mixtures thereof.

In at least one embodiment, the pasty compound is a polymer, such as a hydrocarbon-based polymer.

At least one embodiment of the present disclosure comprises a silicone and fluoro pasty compound that is polymethyl trifluoropropyl methylalkyl dimethylsiloxane, sold under the name X22-1088 by Shin-Etsu.

When the pasty compound is a silicone and/or fluoro polymer, the composition may comprise a compatibilizer such as short-chain esters, for instance isodecyl neopentanoate.

Among the liposoluble polyethers that may be used according to at least one embodiment of the present disclosure, non-limiting mention may be made of copolymers of ethylene oxide and/or of propylene oxide with $C_6$-$C_{30}$ long-chain alkylene oxides, including those copolymers such that the weight ratio of the ethylene oxide and/or of the propylene oxide to the alkylene oxides in the copolymer is from 5:95 to 70:30. In this family, further non-limiting mention may be made of copolymers such that the long-chain alkylene oxides are arranged in blocks with an average molecular weight of from 1000 to 10,000, for example a polyoxyethylene/polydodecyl glycol block copolymer such as the ethers of dodecanediol (22 mol) and of polyethylene glycol (45 EO) sold under the brand name ELFACOS ST9 by Akzo Nobel.

Among the esters that may be used according to at least one embodiment of the present disclosure, non-limiting mention may be made of:
  esters of a glycerol oligomer, such as diglycerol esters, including condensates of adipic acid and of glycerol, for which some of the hydroxyl groups of the glycerols may have reacted with a mixture of fatty acids such as stearic acid, capric acid, stearic acid and isostearic acid and 12-hydroxystearic acid, for instance those sold under the brand name SOFTISAN 649 by the company Sasol,
  phytosterol esters,
  pentaerythritol esters,
  esters formed from:
    at least one alcohol, at least one of the alcohols being a Guerbet alcohol, and
    a diacid dimer formed from at least one unsaturated fatty acid, for instance the ester of fatty acid dimer of tall oil containing 36 carbon atoms and of a mixture i) of Guerbet alcohols containing 32 carbon atoms and ii) of behenyl alcohol; the ester of linoleic acid dimer and of a mixture of two Guerbet alcohols, 2-tetradecyloctadecanol (32 carbon atoms) and 2-hexadecyleicosanol (36 carbon atoms),
  non-crosslinked polyesters resulting from polycondensation between a linear or branched $C_4$-$C_{50}$ dicarboxylic acid or polycarboxylic acid and a $C_2$-$C_{50}$ diol or polyol,
  polyesters resulting from the esterification, with a polycarboxylic acid, of an aliphatic hydroxycarboxylic acid ester, for instance RISOCAST DA-L and RISOCAST DA-H sold by the Japanese company Kokyu Alcohol Kogyo, which are esters resulting from the esterification reaction of hydrogenated castor oil with dilinoleic acid or isostearic acid,
  aliphatic esters of an ester resulting from the esterification of an aliphatic hydroxycarboxylic acid ester with an aliphatic carboxylic acid; (SALACOS HCIS (V)-L sold by the company Nishing Oil).

The aliphatic carboxylic acid contains from 4 to 30 carbon atoms, such as from 8 to 30 carbon atoms. In at least one embodiment, the aliphatic carboxylic acid is chosen from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid and docosanoic acid, and mixtures thereof.

In at least one embodiment, the aliphatic carboxylic acid is branched.

According to at least one embodiment of the present disclosure, the aliphatic hydroxycarboxylic acid ester is derived from a hydroxylated aliphatic carboxylic acid containing from 2 to 40 carbon atoms, such as from 10 to 34 carbon atoms or from 12 to 28 carbon atoms, and from 1 to 20 hydroxyl groups, such as, for example, from 1 to 10 hydroxyl groups or from 1 to 6 hydroxyl groups. The aliphatic hydroxycarboxylic acid ester may be chosen from:
  a) partial or total esters of saturated linear monohydroxylated aliphatic monocarboxylic acids;
  b) partial or total esters of unsaturated monohydroxylated aliphatic monocarboxylic acids;
  c) partial or total esters of saturated monohydroxylated aliphatic polycarboxylic acids;
  d) partial or total esters of saturated polyhydroxylated aliphatic polycarboxylic acids;
  e) partial or total esters of $C_2$ to $C_{16}$ aliphatic polyols that have reacted with a monohydroxylated or polyhydroxylated aliphatic monocarboxylic or polycarboxylic acid, and mixtures thereof.

The aliphatic esters of an ester according to at least one embodiment may be chosen from:
  the ester resulting from the esterification reaction of hydrogenated castor oil with isostearic acid in proportions of 1 to 1 (1/1) or hydrogenated castor oil monoisostearate,
  the ester resulting from the esterification reaction of hydrogenated castor oil with isostearic acid in proportions of 1 to 2 (1/2) or hydrogenated castor oil diisostearate,
  the ester resulting from the esterification reaction of hydrogenated castor oil with isostearic acid in proportions of 1 to 3 (1/3) or hydrogenated castor oil triisostearate,
  and mixtures thereof.

In at least one embodiment of the present disclosure, the pasty compound is present in an amount ranging from 0.5% to 85% by weight, such as, for example, from 1% to 60%, from 2% to 30%, or from 5% to 15% by weight, relative to the total weight of the composition.

Aqueous Phase

The composition according to at least one embodiment of the present disclosure may comprise an aqueous phase, which may comprise water or a mixture of water and of water-miscible solvent (miscibility in water of greater than 50% by weight at 25° C.), for example lower monoalcohols containing from 1 to 5 carbon atoms, such as ethanol or isopropanol, glycols containing from 2 to 8 carbon atoms, such as propylene glycol, ethylene glycol, 1,3-butylene glycol, or dipropylene glycol, $C_3$-$C_4$ ketones and $C_2$-$C_4$ aldehydes, and mixtures thereof.

According to at least one embodiment, the composition comprises an aqueous phase present in an amount less than 10% by weight, such as, for example, less than 5% by weight or less than 2% by weight, relative to the total weight of the composition.

According to at least one other embodiment, the composition comprises an aqueous phase in an amount ranging from 5% to 95% by weight, such as, from 10% to 80% by weight or from 15% to 60% by weight, relative to the total weight of the composition.

Emulsifying System

In at least one embodiment, the composition according to the present disclosure may contain emulsifying surfactants in an amount ranging from 0.01% to 30% by weight, such as, for example, from 1% to 15% or from 2% to 10% by weight, relative to the total weight of the composition.

According to at least one embodiment of the present disclosure, an emulsifier appropriately chosen to obtain an oil-in-water emulsion is used. In at least one further embodiment, an emulsifier having at 25° C. an HLB (hydrophilic-lipophilic balance), in the Griffin sense, of greater than or equal to 8 may be used.

The HLB value according to Griffin is defined in J. Soc. Cosm. Chem. 1954 (volume 5), pages 249-256.

In at least one embodiment, these surfactants may be chosen from nonionic, anionic, cationic and amphoteric surfactants or combinations thereof. Reference may be made to the document "Encyclopedia of Chemical Technology, Kirk-Othmer," volume 22, pp. 333-432, 3rd edition, 1979, Wiley, for the definition of the properties and (emulsifying) functions of surfactants, including pp. 347-377 of this reference, for anionic, amphoteric and nonionic surfactants.

Hydrophilic Gelling Agent

In at least one embodiment, the composition according to the present disclosure may comprise at least one hydrophilic gelling agent when it comprises an aqueous phase.

According to at least one embodiment, hydrophilic gelling agents that may be used in the compositions according to the present disclosure may be chosen from:

- homopolymers or copolymers of acrylic or methacrylic acid or the salts and esters thereof, and, for example, the products sold under the names Versicol F® or Versicol K® by the company Allied Colloid, Ultrahold 8® by the company Ciba-Geigy, and the polyacrylic acids of Synthalen K type;
- copolymers of acrylic acid and of acrylamide sold in the form of the sodium salt thereof under the name Reten® by the company Hercules, sodium polymethacrylate sold under the name Darvan 7® by the company Vanderbilt, and the sodium salts of polyhydroxycarboxylic acids sold under the name Hydagen F® by the company Henkel;
- polyacrylic acid/alkyl acrylate copolymers of the Pemulen type;
- AMPS (polyacrylamidomethylpropanesulfonic acid partially neutralized with ammonia and highly crosslinked) sold by the company Clariant;
- AMPS/acrylamide copolymers of the Sepigel® or Simulgel® type, sold by the company SEPPIC, and
- AMPS/polyoxyethylenated alkyl methacrylate copolymers (crosslinked or non-crosslinked), and mixtures thereof.

The water-soluble film-forming polymers mentioned above may also act as hydrophilic gelling agents.

In at least one embodiment, the at least one hydrophilic gelling agent may be present in a solids content ranging from 0.01% to 30% by weight, such as, for example, from 0.5% to 20% by weight or from 1% to 15% by weight, relative to the total weight of the composition.

Film-Forming Polymer

According to at least one embodiment, the composition according to the present disclosure may comprise at least one film-forming polymer.

The at least one film-forming polymer may be present in the composition according to the disclosure in a solids (or active material) content ranging from 0.1% to 30% by weight, such as, for example, from 0.5% to 20% or from 1% to 15% by weight, relative to the total weight of the composition.

In the present disclosure, the expression "film-forming polymer" means a polymer that is capable, by itself or in the presence of an auxiliary film-forming agent, of forming a macroscopically continuous film that adheres to the eyelashes, such as a cohesive film or a film whose cohesion and mechanical properties are such that the film can be isolated and manipulated separately, for example when the film is made by casting on a non-stick surface, for instance a Teflon-coated or silicone-coated surface.

Among the film-forming polymers that may be used in the composition of the present disclosure, non-limiting mention may be made of synthetic polymers, of free-radical type or of polycondensate type, and polymers of natural origin, and mixtures thereof.

The expression "free-radical film-forming polymer," as used herein, means a polymer obtained by polymerization of unsaturated, including ethylenically unsaturated monomers, each monomer being capable of homopolymerizing (unlike polycondensates).

The film-forming polymers of free-radical type may be, for example, vinyl polymers or copolymers, including acrylic polymers.

The vinyl film-forming polymers may result from the polymerization of ethylenically unsaturated monomers containing at least one acidic group and/or esters of these acidic monomers and/or amides of these acidic monomers.

Monomers bearing an acidic group which may be used according to at least one embodiment include $\alpha,\beta$-ethylenic unsaturated carboxylic acids such as acrylic acid, methacrylic acid, crotonic acid, maleic acid or itaconic acid. In at least one further embodiment, (meth)acrylic acid and crotonic acid are used. In at least one embodiment, (meth)acrylic acid is used.

According to at least one embodiment, the esters of acidic monomers are chosen from (meth)acrylic acid esters (also known as (meth)acrylates), including (meth)acrylates of an alkyl, such as a $C_1$-$C_{30}$ or $C_1$-$C_{20}$ alkyl, (meth)acrylates of an aryl, for example a $C_6$-$C_{10}$ aryl, and (meth)acrylates of a hydroxyalkyl, such as a $C_2$-$C_6$ hydroxyalkyl.

Among the alkyl (meth)acrylates that may be used according to at least one embodiment of the present disclosure, non-limiting mention may be made of methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl (meth)acrylates that may be used according to at least one embodiment of the present disclosure, non-limiting mention may be made of hydroxyethyl acrylate, 2-hydroxypropyl acrylate, hydroxyethyl methacrylate and 2-hydroxypropyl methacrylate.

Among the aryl (meth)acrylates that may be used according to at least one embodiment of the present disclosure, non-limiting mention may be made of benzyl acrylate and phenyl acrylate.

In at least one embodiment, the (meth)acrylic acid esters are alkyl (meth)acrylates.

According to the present disclosure, the alkyl group of the esters may be either fluorinated or perfluorinated, i.e., some or all of the hydrogen atoms of the alkyl group are substituted with fluorine atoms.

Non-limiting examples of amides of the acid monomers that may be mentioned include (meth)acrylamides, such as N-alkyl(meth)acrylamides, for example of a $C_2$-$C_{12}$ alkyl.

Among the N-alkyl(meth)acrylamides that may be used according to at least one embodiment of the present disclosure, non-limiting mention may be made of N-ethylacrylamide, N-t-butylacrylamide, N-t-octylacrylamide and N-undecylacrylamide.

The vinyl film-forming polymers may also result from the homopolymerization or copolymerization of monomers chosen from vinyl esters and styrene monomers. In at least one embodiment, these monomers may be polymerized with acid monomers and/or esters thereof and/or amides thereof, such as those mentioned above.

Non-limiting examples of vinyl esters that may be mentioned include vinyl acetate, vinyl neodecanoate, vinyl pivalate, vinyl benzoate and vinyl t-butylbenzoate.

Non-limiting examples of styrene monomers that may be mentioned include styrene and α-methylstyrene.

Among the film-forming polycondensates that may be used according to at least one embodiment, non-limiting mention may be made of polyurethanes, polyesters, polyesteramides, polyamides, epoxyester resins and polyureas.

The polyurethanes may be chosen from anionic, cationic, nonionic and amphoteric polyurethanes, polyurethane-acrylics, polyurethane-polyvinylpyrrolidones, polyester-polyurethanes, polyether-polyurethanes, polyureas and polyurea/polyurethanes, and mixtures thereof.

The polyesters may be obtained, in a known manner, by polycondensation of dicarboxylic acids with polyols, such as diols.

The dicarboxylic acid may be aliphatic, alicyclic or aromatic. Non-limiting examples of such acids that may be mentioned include: oxalic acid, malonic acid, dimethylmalonic acid, succinic acid, glutaric acid, adipic acid, pimelic acid, 2,2-dimethylglutaric acid, azeleic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid or 2,6-naphthalenedicarboxylic acid. These dicarboxylic acid monomers may be used alone or as a combination of at least two dicarboxylic acid monomers. Among these monomers, in at least one embodiment, the monomers are chosen from phthalic acid, isophthalic acid and terephthalic acid.

The diol may be chosen from aliphatic, alicyclic and aromatic diols. In at least one embodiment, the diol is chosen from: ethylene glycol, diethylene glycol, triethylene glycol, 1,3-propanediol, cyclohexanedimethanol and 4-butanediol. Other polyols that may be used include glycerol, pentaerythritol, sorbitol and trimethylolpropane.

The polyesteramides may be obtained in a manner analogous to that of the polyesters, by polycondensation of diacids with diamines or amino alcohols. Diamines that may be used are ethylenediamine, hexamethylenediamine and meta- or para-phenylenediamine. An amino alcohol that may be used is monoethanolamine.

The polyester may also comprise at least one monomer bearing at least one group —$SO_3M$, wherein M is chosen from a hydrogen atom, an ammonium ion $NH_4^+$ and a metal ion such as, for example, an $Na^+$, $Li^+$, $K^+$, $Mg^{2+}$, $Ca^{2+}$, $Cu^{2+}$, $Fe^{2+}$ or $Fe^{3+}$ ion. A difunctional aromatic monomer comprising such a group —$SO_3M$ may be used in at least one embodiment.

The aromatic nucleus of the difunctional aromatic monomer also bearing a group —$SO_3M$ as described above may be chosen, for example, from benzene, naphthalene, anthracene, biphenyl, oxybiphenyl, sulfonylbiphenyl and methylenebiphenyl nuclei. As examples of difunctional aromatic monomers also bearing a group —$SO_3M$, non-limiting mention may be made of: sulfoisophthalic acid, sulfoterephthalic acid, sulfophthalic acid, 4-sulfonaphthalene-2,7-dicarboxylic acid.

The copolymers used in at least one embodiment are those based on isophthalate/sulfoisophthalate, and, for example, copolymers obtained by condensation of diethylene glycol, cyclohexanedimethanol, isophthalic acid and sulfoisophthalic acid.

The polymers of natural origin, optionally modified, may be chosen from shellac resin, sandarac gum, dammar resins, elemi gums, copal resins and cellulose polymers, and mixtures thereof.

According to at least one embodiment of the composition according to the present disclosure, the film-forming polymer may be a water-soluble polymer and may be present in an aqueous phase of the composition; the polymer is thus solubilized in the aqueous phase of the composition.

According to at least one other embodiment of the composition according to the present disclosure, the film-forming polymer may be a polymer dissolved in a liquid fatty phase comprising organic solvents or oils such as those described above (the film-forming polymer is then said to be a liposoluble polymer).

In at least one embodiment, the liquid fatty phase comprises a volatile oil, optionally mixed with a non-volatile oil, the oils being chosen from, for example, those mentioned above.

Non-limiting examples of liposoluble polymers which may be mentioned include copolymers of vinyl ester (the vinyl group being directly linked to the oxygen atom of the ester group and the vinyl ester containing a saturated, linear or branched hydrocarbon-based radical of 1 to 19 carbon atoms, linked to the carbonyl of the ester group) and of at least one other monomer which may be a vinyl ester (other than the vinyl ester already present), an α-olefin (containing from 8 to 28 carbon atoms), an alkyl vinyl ether (wherein the alkyl group comprises from 2 to 18 carbon atoms) or an allylic or methallylic ester (containing a saturated, linear or branched hydrocarbon-based radical of 1 to 19 carbon atoms, linked to the carbonyl of the ester group).

These copolymers may be crosslinked with the aid of crosslinking agents, which may be either of the vinyl type or of the allylic or methallylic type, such as tetraallyloxyethane, divinylbenzene, divinyl octanedioate, divinyl dodecanedioate and divinyl octadecanedioate.

Non-limiting examples of these copolymers that may be mentioned include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Non-limiting examples of liposoluble film-forming polymers which may also be mentioned include liposoluble copolymers, such as those resulting from the copolymerization of vinyl esters containing from 9 to 22 carbon atoms or of alkyl acrylates or methacrylates, and alkyl radicals containing from 10 to 20 carbon atoms.

Such liposoluble copolymers may be chosen from polyvinyl stearate, polyvinyl stearate crosslinked with the aid of divinylbenzene, of diallyl ether or of diallyl phthalate, polystearyl (meth)acrylate, polyvinyl laurate and polylauryl (meth)acrylate, it being possible for these poly(meth)acrylates to be crosslinked with the aid of ethylene glycol dimethacrylate or tetraethylene glycol dimethacrylate.

The liposoluble copolymers defined above are known and are described, for example, in French Patent Application No. FR-A-2 232 303. In at least one embodiment, they may have a weight-average molecular weight ranging from 2000 to 500,000, such as, for example, from 4000 to 200,000.

As liposoluble film-forming polymers which may be used in the present disclosure, non-limiting mention may also be made of polyalkylenes, for example copolymers of $C_2$-$C_{20}$ alkenes, such as polybutene, alkylcelluloses with a linear or branched, saturated or unsaturated $C_1$-$C_8$ alkyl radical, for instance ethylcellulose and propylcellulose, copolymers of vinylpyrrolidone (VP) and, for example, copolymers of vinylpyrrolidone and of $C_2$ to $C_{40}$ or $C_3$ to $C_{20}$ alkenes. As examples of VP copolymers which may be used in the present disclosure, non-limiting mention may be made of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

Non-limiting mention may also be made of silicone resins, which can be soluble or swellable in silicone oils, which are crosslinked polyorganosiloxane polymers. The nomenclature of silicone resins is known under the name "MDTQ," with the resin being described as a function of the various siloxane monomer units it comprises, each of the letters "MDTQ" characterizing a type of unit.

Non-limiting examples of commercially available polymethylsilsesquioxane resins that may be mentioned include those sold:
  by the company Wacker under the reference RESIN MK, such as BELSIL PMS MK; and
  by the company Shin-Etsu under the reference KR-220L.

Siloxysilicate resins that may be used according to at least one embodiment, include trimethyl siloxysilicate (TMS) resins such as those sold under the reference SR 1000 by the company General Electric or under the reference TMS 803 by the company Wacker. Non-limiting mention may also be made of the trimethyl siloxysilicate resins sold in a solvent such as cyclomethicone, sold under the name KF-7312J by the company Shin-Etsu, and DC 749 and DC 593 by the company Dow Corning.

Non-limiting mention may also be made of silicone resin copolymers such as those mentioned above with polydimethylsiloxanes, for instance the pressure-sensitive adhesive copolymers sold by the company Dow Corning under the reference Bio-PSA and described in U.S. Pat. No. 5,162,410, or the silicone copolymers derived from the reaction of a silicone resin, such as those described above, and of a diorganosiloxane, as described in International Patent Application No. WO 2004/073626.

According to at least one embodiment of the present disclosure, the film-forming polymer is a film-forming linear block ethylenic polymer, which may comprise at least one first block and at least one second block with different glass transition temperatures (Tg), the at least one first and second blocks being linked together via an intermediate block comprising at least one constituent monomer of the first block and at least one constituent monomer of the second block.

In at least one embodiment, the at least one first and second blocks of the block polymer are mutually incompatible.

Such polymers are described, for example, in European Patent No. EP 1 411 069 or International Patent Application No. WO 04/028488.

The film-forming polymer may also be present in the composition in the form of particles dispersed in an aqueous phase or in a non-aqueous solvent phase, which is generally known as a latex or pseudolatex. The techniques for preparing these dispersions are well known to those skilled in the art.

Non-limiting examples of aqueous dispersions of film-forming polymers that may be used include the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® or Daitosol 5000 SJ® by the company Daito Kasey Kogyo; Syntran 5760® by the company Interpolymer, Allianz OPT by the company Rohm & Haas, aqueous dispersions of acrylic or styrene/acrylic polymers sold under the brand name Joncryl® by the company Johnson Polymer, or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer; the sulfopolyesters sold under the brand name Eastman AQ® by the company Eastman Chemical Products, and vinyl dispersions, for instance Mexomer PAM® from the company Chimex, and mixtures thereof.

Non-limiting examples of non-aqueous film-forming polymer dispersions that may also be mentioned include acrylic dispersions in isododecane, for instance Mexomer PAP® from the company Chimex, and dispersions of particles of a grafted ethylenic polymer, such as an acrylic polymer, in a liquid fatty phase, the ethylenic polymer, for example, being dispersed in the absence of additional stabilizer at the surface of the particles as described in International Patent Application No. WO 04/055081.

The composition according to at least one embodiment of the present disclosure may comprise a plasticizer that promotes the formation of a film with the film-forming polymer. Such a plasticizer may be chosen from any compound known to those skilled in the art as being capable of fulfilling the desired function.

Dyestuff

In at least one embodiment of the present disclosure, the composition may also comprise at least one dyestuff, for instance pulverulent dyes, liposoluble dyes and water-soluble dyes.

Pulverulent dyestuffs may be chosen from pigments and nacres.

The pigments may be white or colored, mineral and/or organic, and coated or uncoated. Among the mineral pigments that may be used according to at least one embodiment, non-limiting mention may be made of titanium dioxide, optionally surface-treated, zirconium oxide, zinc oxide or cerium oxide, and also iron oxide or chromium oxide, manganese violet, ultramarine blue, chromium hydrate and ferric blue. Among non-limiting examples of organic pigments that may used according to the present disclosure, non-limiting mention may be made of carbon black, pigments of D&C type, and lakes based on cochineal carmine or on barium, strontium, calcium or aluminum.

The nacres may be chosen from white nacreous pigments such as mica coated with titanium or with bismuth oxychloride, colored nacreous pigments such as titanium mica with iron oxides, titanium mica with, for example, ferric blue or chromium oxide, titanium mica with an organic pigment of the abovementioned type, and also nacreous pigments based on bismuth oxychloride.

The liposoluble dyes may be chosen from, for example, Sudan Red, D&C Red 17, D&C Green 6, β-carotene, soybean oil, Sudan Brown, D&C Yellow 11, D&C Violet 2, D&C Orange 5, quinoline yellow and annatto.

In at least one embodiment, these dyestuffs may be present in an amount ranging from 0.01% to 30% by weight relative to the total weight of the composition.

Fillers

According to at least one embodiment, the composition according to the present disclosure may also comprise at least one filler.

The fillers may be chosen from those that are well known to those skilled in the art and commonly used in cosmetic compositions. The fillers may be mineral or organic, and lamellar or spherical. Non-limiting mention may be made of talc, mica, silica, kaolin, polyamide powders, for instance the Nylon® sold under the trade name Orgasol® by the company Atochem, poly-β-alanine powders and polyethylene powders, powders of tetrafluoroethylene polymers, for instance Teflon®, lauroyllysine, starch, boron nitride, expanded polymeric hollow microspheres such as those of polyvinylidene chloride/acrylonitrile, for instance the products sold under the name Expancel® by the company Nobel Industrie, acrylic powders, such as those sold under the name Polytrap® by the company Dow Corning, polymethyl methacrylate particles and silicone resin microbeads (for example Tospearls® from Toshiba), precipitated calcium carbonate, magnesium carbonate and magnesium hydrocarbonate, hydroxyapatite, hollow silica microspheres (Silica Beads® from Maprecos), glass or ceramic microcapsules, metal soaps derived from organic carboxylic acids containing from 8 to 22 carbon atoms, such as from 12 to 18 carbon atoms, for example zinc, magnesium or lithium stearate, zinc laurate and magnesium myristate.

In at least one embodiment a compound may be used that is capable of swelling on heating, including heat-expandable particles such as non-expanded microspheres of copolymer of vinylidene chloride/acrylonitrile/methyl methacrylate or of acrylonitrile homopolymer copolymer, for instance those sold, respectively, under the references Expancel® 820 DU 40 and Expancel® 007WU by the company Akzo Nobel.

In at least one embodiment, the fillers may be present in an amount ranging from 0.1% to 25% by weight, such as, for example, from 1% to 20% by weight, relative to the total weight of the composition.

The coloring agent or the filler may also be present in the form of a "particulate paste."

When it contains particles that are solid at room temperature, the composition according to the disclosure can be prepared by introducing them into the composition in the form of a colloidal dispersion, also known as a "particulate paste," as described in International Patent Application No. WO 02/39961, the content of which is incorporated herein by reference.

For the purposes of the present disclosure, the expressions "colloidal dispersion" and "particulate paste" mean a concentrated colloidal dispersion of coated or uncoated particles in a continuous medium that are stabilized using a dispersant or optionally without a dispersant. These particles may be chosen from pigments, nacres and solid fillers, and mixtures thereof. These particles may be in any form, such as, for example, spherical or elongated form like fibers. They are insoluble in the medium.

The dispersant serves to protect the dispersed particles against their aggregation or flocculation. In at least one embodiment, the dispersant used to stabilize a colloidal dispersion is present in an amount ranging from 0.3 to 5 mg/m$^2$, such as, for example, from 0.5 to 4 mg/m$^2$, of surface area of particles. This dispersant may be a surfactant, an oligomer, a polymer or a mixture of several of them, bearing at least one functionality having a strong affinity for the surface of the particles to be dispersed. For example, they may attach physically or chemically to the surface of the pigments. These dispersants may also contain at least one functional group that is compatible with or soluble in the continuous medium. In at least one embodiment, esters of 12-hydroxystearic acid and of a $C_8$ to $C_{20}$ fatty acid and of a polyol, for instance glycerol or diglycerol, are used, such as the stearate of poly(12-hydroxystearic acid) with a molecular weight of about 750 g/mol, such as the product sold under the name SOLSPERSE 21 000 by the company Avecia, the polyglyceryl-2 dipolyhydroxystearate (CTFA name) sold under the reference DEHYMYLS PGPH by the company Henkel or polyhydroxystearic acid, such as the product sold under the reference ARLACEL P100 by the company Uniqema, and mixtures thereof.

As other dispersants which may be used in the composition of the present disclosure, non-limiting mention may be made of quaternary ammonium derivatives of polycondensed fatty acids, for instance SOLSPERSE 17 000 sold by the company Avecia, and mixtures of polydimethylsiloxane/oxypropylene, such as those sold by the company Dow Corning under the references DC2-5185 and DC2-5225 C.

In at least one embodiment, polydihydroxystearic acid and the 12-hydroxystearic acid esters can be used for a hydrocarbon-based or fluorinated medium, whereas the mixtures of oxyethylenated/oxypropylenated dimethylsiloxane can be used for a silicone medium.

The colloidal dispersion is a suspension of particles that are, for example, micron-sized (<10 μm) in a continuous medium. In at least one embodiment, the volume fraction of particles in a concentrated dispersion ranges from 20% to 40%, or, for example, greater than 30%, which corresponds to a weight content that may be up to 70% depending on the density of the particles.

The particles dispersed in the medium may comprise mineral or organic particles or mixtures thereof, such as those described below.

The continuous medium of the paste may be of any nature and may contain any solvent or liquid fatty substance and mixtures thereof. In at least one embodiment, the liquid medium of the particulate paste is one of the liquid fatty substances or oils that can be used in the composition, thus forming part of the liquid fatty phase.

According to at least one embodiment, the "particulate paste" or colloidal dispersion is a "pigmentary paste" containing a colloidal dispersion of coated or uncoated colored particles. These colored particles can be pigments, nacres or a mixture of pigments and/or nacres.

In at least one embodiment, the colloidal dispersion is present in an amount ranging from 0.5% to 30% by weight, such as, for example, from 2% to 20% or from 2% to 15% by weight, relative to the total weight of the composition.

The composition of the disclosure may also comprise at least one additive usually used in cosmetics, such as antioxidants, preserving agents, fibers, fragrances, neutralizers, thickeners, vitamins, moisturizers, screening agents and in particular sunscreens, coalescers and plasticizers, and mixtures thereof.

Needless to say, a person skilled in the art will take care to select the optional additional additives and/or the amount thereof such that the advantageous properties of the composition according to the disclosure are not, or are not substantially, adversely affected by the envisaged addition of the optional at least one additive.

The compositions according to the disclosure may be prepared according to methods known to those skilled in the art.

The composition used in the process according to the disclosure may be packaged, for example, in a packaging and application device comprising:
  i) a support;
  ii) an at least partially convex application surface arranged on one face of the support, the application surface being formed from at least part of the side surface of a stick of the composition; and
  iii) a plurality of application members, for example in the form of a teeth or hairs, arranged in at least one row extending from at least one side of the application surface, and protruding relative to the face of the support.

A preferred packaging device is shown in FIG. 1, which is shown merely as a guide and does not in any way limit the disclosure. FIG. 1 shows a profile view in perspective of one embodiment of a device according to the present disclosure.

The device 1 comprises a handle member 2 on which is retained a support 3 presenting the application member 4 which extends along a longitudinal axis X. Device 1 comprises a longitudinal wall 16.

Application member 4 is cylindrical and comprises the composition in stick form. Application member 4 comprises an application surface 6 that can be placed in contact with keratin fibers without any portion of support 3 coming into contact with the keratin fibers.

Application member 4 rests on one face of support 3 and is retained thereon, for example, by fixing means such as a ring 23. To protect application surface 6 and application member 4 between uses, a removable closing cap (not shown) can be mounted around support 3 and, for example, retained thereon. The application member 4 may, as shown in FIG. 1, project beyond the axial end 24 of the support 3 so as to have an axial end 50 forming an extension of application surface 6.

Support 3 comprises a row 5 of application members 9 projecting from a longitudinal side edge 8 and extending laterally along application member 4, for example against the outer edge of one part of application member 4. Application surface 6 is thus accessible beyond the free ends 10 of application members 9 and also in the spaces between application members 9.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the invention as approximations, the numerical values set forth in the specific examples are reported as precisely as possible. Any numerical value, however, inherently contains certain errors necessarily resulting from the standard deviation found in its respective testing measurement.

The examples that follow are intended to illustrate the invention without, however, being limiting in nature. Unless otherwise indicated, the amounts are given in grams.

EXAMPLE 1

| | |
|---|---|
| Sucrose acetate isobutyrate (Eastman SAIB sold by Eastman Chemical) | 5 |
| Mixture of linear-chain fatty alcohol (C30-C50) and of C30-C50 hydrocarbons (80/20) (Performacol 550L from New Phase Technologies) | 2.5 |
| Polyethylene wax (Polyethylene Wax AC 617 from Honeywell) | 10.5 |
| Dispersion of poly(methyl methacrylate/acrylic acid) particles surface-stabilized in isododecane with a polystyrene/copoly (ethylene-propylene) diblock copolymer sold under the name Kraton G1701, at a polymer solids content of 24.5% (Mexomer PAP from Chimex) | 67.82 |
| Black iron oxide | 5 |
| Stearate of the oligomer 12-polyhydroxystearic acid (Solsperse 21000 from Avecia) | 0.16 |
| Hydrogenated isoparaffin (6-8 mol of isobutylene) (Parleam from Nippon Oil Fats) | 9 |

Procedure

A pigmentary paste was prepared in the following manner: the Solsperse 21000 was dissolved in the Parleam at about 80° C. over 10-15 minutes and the black iron oxide was then added with stirring using a Rayneri blender for 15 minutes. The mixture was ground using a ball mill for about 40 minutes.

The waxes were then melted with the sucrose acetate isobutyrate, the above pigmentary paste and the polyisobutene at 110° C. in a heating pan for about 45 minutes with stirring using a Rayneri blender.

After homogenization of the mixture, it was cooled to 90° C. and the dispersion of acrylate polymer particles in the isododecane was then added with stirring. After homogenization of the mixture, the fluid was poured into a silicone aluminum mold at 42° C. It was left to stand for 10 minutes, the surface of the sticks was then scraped and the sticks were then placed in a freezer at −28° C. for 45 minutes. After recrystallization, the sticks were removed from the molds and placed in suitable packaging.

This mascara had a hardness, measured according to the protocol indicated hereinabove, of 1814 Pa.

EXAMPLE 2

| | |
|---|---|
| Beeswax | 15 |
| Polyethylene wax (Performalene 500 from NPT) | 0.5 |
| Polymethyl trifluoropropyl dimethylsiloxane (100 cSt) from Shin-Etsu | 8.4 |
| Sucrose acetate isobutyrate (Eastman SAIB sold by Eastman Chemical) | 3 |
| Mixture of linear-chain fatty alcohol (C30-050) and of C30-050 hydrocarbons (80/20) (Performacol 550L from New Phase Technologies) | 2.5 |
| Phenyltrimethylsiloxytrisiloxane (20 cSt) (DC556 from Dow Corning) | 2.6 |
| Cyclopentadimethylsiloxane (DC 245 Fluid from Dow Corning) | 58.5 |
| Stearate of the oligomer 12-polyhydroxystearic acid (Solsperse 21000 from Avecia) | 0.174 |

-continued

| | |
|---|---|
| Black iron oxide | 5.22 |
| Hydrogenated isoparaffin (6-8 mol of isobutylene) (Parleam from Nippon Oil Fat) | 7.1 |
| Isododecane | qs 100 |

Procedure

A pigmentary paste was prepared in the following manner: the Solsperse 21000 was dissolved in the Parleam at about 80° C. over 10-15 minutes and the black iron oxide was then added with stirring using a Rayneri blender for 15 minutes. The mixture was ground using a ball mill for about 40 minutes.

The waxes were melted with the sucrose acetate isobutyrate, the above pigmentary paste, the polyisobutene and the phenyltrimethylsiloxytrisiloxane at 110° C. in a heating pan for about 45 minutes with stirring using a Rayneri blender.

After homogenization of the mixture, it was cooled to 90° C. and the polymethyl trifluoropropyl dimethylsiloxane, the cyclopentadimethylsiloxane and the isododecane were then added with stirring using a Rayneri blender.

After homogenization of the mixture, the fluid was poured into a silicone aluminum mold at 42° C. It was left to stand for 10 minutes, the surface of the sticks was then scraped and the sticks were then placed in a freezer at −28° C. for 45 minutes. After recrystallization, the sticks were removed from the molds and placed in suitable packaging.

The mascara of Example 2 had a hardness, measured according to the protocol indicated hereinabove, of 2177 Pa.

What is claimed is:

1. A process for coating keratin fibers, comprising contacting:
    the keratin fibers with at least part of a surface of a stick of a dry-applicable composition wherein the dry-applicable composition, has a hardness ranging from 900 to 10,000 Pa, and comprises:
        at least one liquid fatty phase comprising at least one volatile oil selected from the group consisting of hydrocarbon-based volatile oils containing from 8 to 16 carbon atoms and cyclic silicone volatile oils, wherein the at least one liquid fatty phase is present in an amount ranging from 5% to 85% by weight relative to the total weight of the at least one composition,
        at least one pasty compound, wherein the at least one pasty compound is present in an amount ranging from 0.5% to 85% by weight relative to the total weight of the at least one composition,
        at least one film-forming polymer, wherein the at least one film-forming polymer is present in a solids content ranging from 0.1% to 30% by weight relative to the total weight of the at least one composition,
        at least one dyestuff, wherein the at least one dyestuff is present in an amount ranging from 0.01% to 30% by weight relative to the total weight of the at least one composition,
        at least one structuring agent for the at least one liquid fatty phase which is a structuring wax, and
        at least one non-structuring wax,
    wherein the weight ratio of the at least one structuring wax to the at least one non-structuring wax ranges from 15:85 to 35:65, and
    wherein when an aqueous phase is present in the composition, it is present in an amount less than 2% by weight, relative to the total weight of the composition.

2. The process according to claim 1, wherein the at least one composition has a hardness ranging from 1800 to 8200 Pa.

3. The process according to claim 1, wherein the at least one composition has an evaporation profile such that the mass of the at least one volatile oil evaporated after thirty minutes ranges from 1.7 to 370 mg/cm$^2$.

4. The process according to claim 3, wherein the at least one composition has an evaporation profile such that the mass of the at least one volatile oil evaporated after thirty minutes ranges from 2 to 30 mg/cm$^2$.

5. The process according to claim 1, wherein the at least one liquid fatty phase is present in an amount ranging from 15% to 60% by weight, relative to the total weight of the at least one composition.

6. The process according to claim 1, wherein the at least one structuring agent is present in an amount ranging from 1% to 50% by weight, relative to the total weight of the at least one composition.

7. The process according to claim 6, wherein the at least one structuring agent is present in an amount ranging from 7.5% to 17% by weight, relative to the total weight of the at least one composition.

8. The process according to claim 1, wherein the at least one structuring wax is chosen from polar waxes and apolar waxes.

9. The process according to claim 1, wherein the at least one non-structuring wax is chosen from polar waxes and apolar waxes.

10. The process according to claim 1, wherein the at least one structuring wax and the at least one non-structuring wax are present in a total amount ranging from 1% to 30% by weight, relative to the total weight of the at least one composition.

11. The process according to claim 10, wherein the at least one structuring wax and the at least one non-structuring wax are present in a total amount ranging from 7.5% to 17% by weight, relative to the total weight of the at least one composition.

12. The process according to claim 1, wherein at least one of the at least one structuring wax and at least one non-structuring wax is chosen from aprotic waxes.

13. The process according to claim 12, wherein the at least one aprotic wax is chosen from microcrystalline waxes, paraffin waxes, and polyethylene waxes.

14. The process according to claim 1, wherein at least one of the at least one structuring wax and at least one non-structuring wax is chosen from protic waxes.

15. The process according to claim 14, wherein the at least one protic wax is chosen from beeswax and fatty alcohol waxes containing from 20 to 60 carbon atoms.

16. The process according to claim 1, wherein the at least one composition comprises at least one polyethylene wax, at least one fatty alcohol wax, and at least one volatile hydrocarbon-based oil chosen from isoparaffins containing from 8 to 16 carbon atoms.

17. The process according to claim 1, wherein the at least one composition comprises at least one polyethylene wax, at least one beeswax, and at least one volatile silicone oil chosen from volatile cyclic silicone oils.

18. The process according to claim 17, wherein the at least one volatile cyclic silicone oil has a viscosity <8 centistokes ($8 \times 10^{-6}$ m$^2$/s).

19. The process according to claim 1, wherein the at least one pasty compound is present in an amount ranging from 5% to 15% by weight, relative to the total weight of the at least one composition.

20. The process according to claim 1, wherein the at least one film-forming polymer is present in a solids content ranging from 1% to 15% by weight, relative to the total weight of the at least one composition.

21. A process for coating keratin fibers, comprising:
contacting the keratin fibers with at least part of the surface of a stick of a dry-applicable composition; and
causing a relative displacement between the surface of the stick of the dry-applicable composition and the keratin fibers so as to bring about erosion the composition and application to the keratin fibers in the form of a deposit of at least one coat,
wherein the dry-applicable composition comprises:
at least one liquid fatty phase comprising at least one volatile oil selected from the group consisting of hydrocarbon-based volatile oils containing from 8 to 16 carbon atoms and cyclic silicone volatile oils, wherein the at least one liquid fatty phase is present in an amount ranging from 5% to 85% by weight relative to the total weight of the at least one composition,
at least one pasty compound, wherein the at least one pasty compound is present in an amount ranging from 0.5% to 85% by weight relative to the total weight of the at least one composition,
at least one film-forming polymer, wherein the at least one film-forming polymer is present in a solids content ranging from 0.1% to 30% by weight relative to the total weight of the at least one composition,
at least one dyestuff, wherein the at least one dyestuff is present in an amount ranging from 0.01% to 30% by weight relative to the total weight of the at least one composition,
at least one structuring agent for the at least one liquid fatty phase which is a structuring wax, and
at least one non-structuring wax,
wherein the weight ratio of the at least one structuring wax to the at least one non-structuring wax ranges from 15:85 to 35:65, and
wherein when an aqueous phase is present in the composition, it is present in an amount less than 2% by weight, relative to the total weight of the composition.

22. The process according to claim 21, wherein the dry-applicable composition has a hardness ranging from 500 to 18,200 Pa.

23. The process according to claim 22, wherein the dry-applicable composition has a hardness ranging from 1800 to 8200 Pa.

* * * * *

UNITED STATES PATENT AND TRADEMARK OFFICE
CERTIFICATE OF CORRECTION

PATENT NO. : 8,460,645 B2  
APPLICATION NO. : 13/209615  
DATED : June 11, 2013  
INVENTOR(S) : Nathalie Jager Lezer et al.

Page 1 of 1

It is certified that error appears in the above-identified patent and that said Letters Patent is hereby corrected as shown below:

In the Claims

Column 27, line 37, claim 1, "composition wherein" should read --composition, wherein--.

Column 28, line 62, claim 18, "<8 centistokes" should read --≤8 centistokes--.

Signed and Sealed this  
Fifth Day of November, 2013

Teresa Stanek Rea  
*Deputy Director of the United States Patent and Trademark Office*